(12) United States Patent
Wang et al.

(10) Patent No.: US 10,583,298 B2
(45) Date of Patent: Mar. 10, 2020

(54) SYSTEMS AND METHODS FOR NEUROSTIMULATION THERAPY

(71) Applicant: Boston Scientific Scimed, Inc., Maple Grove, MN (US)

(72) Inventors: Jeffrey Wang, Arlington, MA (US); John Edward Sherry, Needham, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 16/018,396

(22) Filed: Jun. 26, 2018

(65) Prior Publication Data

US 2018/0296841 A1    Oct. 18, 2018

Related U.S. Application Data

(62) Division of application No. 14/873,992, filed on Oct. 2, 2015, now Pat. No. 10,035,020.

(60) Provisional application No. 62/059,548, filed on Oct. 3, 2014.

(51) Int. Cl.
*A61N 1/36* (2006.01)
*A61N 1/05* (2006.01)
*A61N 1/372* (2006.01)

(52) U.S. Cl.
CPC ....... *A61N 1/36139* (2013.01); *A61N 1/0551* (2013.01); *A61N 1/36007* (2013.01); *A61N 1/36057* (2013.01); *A61N 1/37247* (2013.01)

(58) Field of Classification Search
CPC ............ A61N 1/36139; A61N 1/37247; A61N 1/0551; A61N 1/36007; A61N 1/36057

USPC .......................................................... 607/40
See application file for complete search history.

(56) References Cited

U.S. PATENT DOCUMENTS

| | | | |
|---|---|---|---|
| 7,389,145 B2 | 6/2008 | Kilgore et al. | |
| 2005/0010260 A1* | 1/2005 | Gerber | A61N 1/36071 607/39 |
| 2007/0027494 A1 | 2/2007 | Gerber | |
| 2011/0118805 A1* | 5/2011 | Wei | A61N 1/36007 607/41 |
| 2012/0197336 A1 | 8/2012 | Su | |

FOREIGN PATENT DOCUMENTS

| | | |
|---|---|---|
| JP | 2008-509794 A | 4/2008 |
| JP | 2008-502707 A | 1/2011 |
| KR | 2008 0052483 A | 6/2008 |
| WO | WO 2013/169896 A2 | 11/2013 |

OTHER PUBLICATIONS

International Search Report and Written Opinion for corresponding International Application No. PCT/US2015/053807, dated Jan. 25, 2016 (7 pages).

(Continued)

*Primary Examiner* — Amanda K Hulbert
*Assistant Examiner* — Philip C Edwards
(74) *Attorney, Agent, or Firm* — Bookoff McAndrews, PLLC

(57) ABSTRACT

The present disclosure pertains to methods, devices and systems for neurological regulation. The methods, devices and systems described herein are useful, for example, in the treatment of conditions of the bladder such as overactive bladder.

20 Claims, 3 Drawing Sheets

(56) References Cited

OTHER PUBLICATIONS

Case Western Reserve University; Department of Biomedical Engineering; Applied Neural Control: J.T. Mortimer, Homepage, Unidirectional propagation (http://www.case.edu/groups/ANCL/pages/02/02_02.htm?nw_view=1290888692&), last accessed Feb. 23, 2016.
Medtronic Bladder Control Overview (http://www.medtronic.com/us-en/patients/treatments-therapies/bladder-control/about/oab.html), last accessed Jul. 17, 2017.
N. Bhadra et al., "Selective block of external anal sphincter activation during electrical stimulation of the sacral anterior roots in a canine model," Neurogastroenterol Motif. Oct. 2005; 17(5):721-6.

* cited by examiner

SYSTEMS AND METHODS FOR NEUROSTIMULATION THERAPY

CROSS-REFERENCE TO RELATED APPLICATIONS

This application is a divisional application of U.S. application Ser. No. 14/873,992, filed Oct. 2, 2015, which claims the benefit of priority from U.S. Provisional Application No. 62/059,548, filed Oct. 3, 2014, the entireties of each are incorporated by reference herein.

TECHNICAL FIELD

The present disclosure relates to systems and methods for neurostimulation therapy, and more particularly systems and methods for overactive bladder therapy.

BACKGROUND

Overactive bladder (OAB) is a problem with bladder-storage function that causes a sudden urge to urinate. The urge may be difficult to stop, and overactive bladder may lead to the involuntary loss of urine (incontinence). Symptoms include: a sudden urge to urinate that's difficult to control, incontinence, frequent urination, and nocturia. The first line of treatments for OAB involves changes in diet, weight control, bladder training and pelvic floor exercises, and medications. If the first line treatments are not effective, then bladder injections, nerve stimulation, and surgery are then considered.

Sacral nerve stimulation is one of the more common stimulation therapies used today to treat OAB. There is only one device that has FDA approval being used today, InterStim™ Therapy developed by Medtronic. InterStim™ is a neuromodulation technique that targets the sacral nerves near the tailbone. These nerves play a role in controlling certain bladder muscles and functions. The therapy involves modulating these nerves, usually the third sacral nerve, through electrical impulses in order to help the brain and nerves communicate properly. This treatment is a two-step process starting with an evaluation process, and then an implantation process if the patient is deemed suitable for the procedure. For the evaluation, the doctor either inserts a temporary thin lead wire near the sacral nerves or a long-term lead that is fully implanted. The lead is connected to an external neurostimulator which generates mild electrical pulses. If the patient passes the evaluation, the doctor typically implants an implantable pulse generator (IPG) in a deep subcutaneous pocket in the right buttock connected to the lead and thus to the sacral nerves.

Currently, about 60% to 80% of patients undergoing sacral nerve stimulation are successful in bladder function improvement. Furthermore, a successful improvement only means a person who has had at least a 50% improvement with OAB. One objective of the present disclosure is to increase the efficacy of idiopathic overactive bladder treatments through nerve stimulation.

SUMMARY

The present disclosure is based on methods, devices and systems for neurological regulation. The methods, devices and systems described herein are useful, for example, in the treatment of conditions of the bladder such as overactive bladder.

In some aspects, methods of treating a patient are provided in which nerve signals are regulated based on pressure readings taken from the bladder. The methods may include: (a) sensing bladder pressure within a urinary bladder of the patient; (b) measuring current arising from neural activity within one or more nerves of the patient; and (c) forming modified electrical signals within the one or more nerves based on sensed bladder pressure and measured current obtained in tasks (a) and (b). In certain examples, the one or more nerves may include one or more sacral nerves. In certain examples, the patient is treated for overactive bladder.

In some examples, natural afferent signals within one or more nerves are at least partially blocked by the modified electrical signals. For example, the modified electrical signals may be in response to a condition wherein the measured current is below a predetermined threshold. In some examples, natural afferent signals in the one or more nerves are unblocked in response to conditions that include a condition wherein the sensed pressure is above a predetermined threshold.

Alternatively or in addition, in some examples, the modified electrical signals may include artificial signals that are introduced into the one or more nerves. For example, artificial signals may be introduced into the one or more nerves in response to conditions including a condition wherein the sensed pressure is above a predetermined threshold.

In some aspects, systems are provided that regulate the nerve signals based on pressure readings from the bladder. For example, such a system may include: a bladder pressure sensor configured to measure and transmit bladder pressure information and a nerve current regulator configured to sense and at least partially block electrical signals transmitted by one or more nerves based on information including bladder pressure information received from the bladder pressure sensor. The bladder pressure sensor may, for example, be configured for attachment to an inner surface of a bladder. The nerve current regulator may, for example, include a lead including at least one electrode configured to sense and modify nerve signals transmitted by the one or more nerves. The nerve current regulator may be configured, for example, to at least partially block electrical signals transmitted by the one or more nerves, by generating uni-directionally propagating action potentials within the one or more nerves.

In some examples, the system may further include an electrical stimulator, a control unit, or both.

Where an electrical stimulator is provided, the electrical stimulator may be configured to introduce stimulating electrical signals into one or more nerves. Where an electrical stimulator is provided, the nerve current regulator and electrical stimulator may be provided within separate devices, or within a single device. Separate leads may be provided for each of the nerve current regulator and the electrical stimulator, or a common lead may be provided for the nerve current regulator and the electrical stimulator.

Where a control unit is provided (e.g., a portable control unit such as a handheld control unit or stationary control unit), the control unit may be configured to receive control input including bladder pressure information from the bladder pressure sensor and may be configured to provide control output including output to the nerve current regulator based on the control input. The output to the nerve current regulator may include, for example, instructions to at least partially block electrical signals transmitted by one or more nerves or instructions to refrain from at least partially blocking electrical signals transmitted by one or more nerves. The control input may further include, for example, patient input (e.g., the control unit may be configured to prompt the patient for patient input including approval to initiate a bladder voiding event, etc.), nerve signal information receivable from the nerve current regulator, or a combination thereof. The control output may further include, for example, output to a control unit display that is viewable by the patient, output to an electrical stimulator (where provided), or a combination thereof.

In some aspects, devices are provided that regulate the nerve signals based on pressure readings from the bladder. For example, a nerve current regulator may be provided which is configured to sense and at least partially block electrical signals transmitted by one or more nerves based on bladder pressure information. The nerve current regulator may be configured to at least partially block electrical signals transmitted by the one or more nerves, for example, by forming unidirectionally propagating action potentials within the one or more nerves.

The details of various aspects, examples, features, and advantages of the present disclosure are set forth in the accompanying drawings and the description below. Other aspects, examples, features, and advantages of the present disclosure will be apparent from the description and drawings, and from the claims.

It may be understood that both the foregoing general description and the following detailed description are exemplary and explanatory only and are not restrictive of the examples, as claimed.

BRIEF DESCRIPTION OF THE DRAWINGS

The accompanying drawings, which are incorporated in and constitute a part of this specification, illustrate exemplary examples of the present disclosure and together with the description, serve to explain the principles of the disclosure.

DETAILED DESCRIPTION

The present disclosure is based on methods, devices and systems for neurostimulation. In various examples, the present disclosure pertains to devices, systems and methods for regulating afferent nerve signals being sent to the brain (e.g., from the bladder to the brain) in order to treat overactive bladder. Current technology for treating overactive bladder merely sends out constant electrical impulses to a patient with the desire that the patient responds well. In examples of the present disclosure, differing electrical signals are sent to the patient at different times.

In various examples, a system may be employed which can sense the pressure of the bladder and based on the bladder pressure, among other parameters, dictate the current that is being sent to the brain, for example, increasing, decreasing, or maintaining the level of current sent to the brain via electrodes disposed proximate the sacral nerves.

In healthy humans, when the bladder is filling, low-level afferent signals are sent to the brain and, once the bladder is full, the intensity of those afferent signals increases, indicating that it is time to void the bladder. In the present disclosure, a nerve current regulator is employed to keep signals being sent to the brain at a low level as the bladder is filling. The purpose of keeping the signals at a low level is to reduce or eliminate urinary frequency by stopping the body from having the urge feeling, allowing the detrusor muscles to remain relaxed and the external urinary sphincter to remain contracted, thereby combating premature urination. The degree of bladder filling may be determined based on readings from the bladder sensor. Once the bladder is full and conditions are ripe for voiding (e.g., the patient is in a position to void the bladder), the signal level being sent to the brain may be increased and the bladder is voided. Signal levels to the brain are controlled using a system that regulates and stimulates nerve current.

Figure 1A:
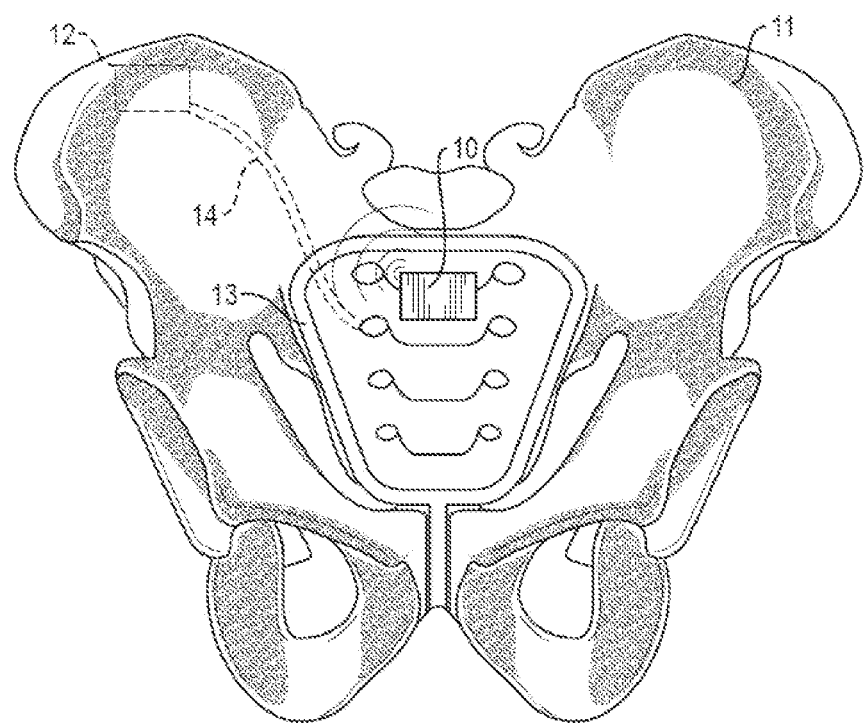
FIGS. 1A and 1B are schematic diagrams illustrating an implantable system, incorporating an implantable sensing device in communication with an implantable regulating and stimulating device, in accordance with an example of the present disclosure.
Figure 1B:
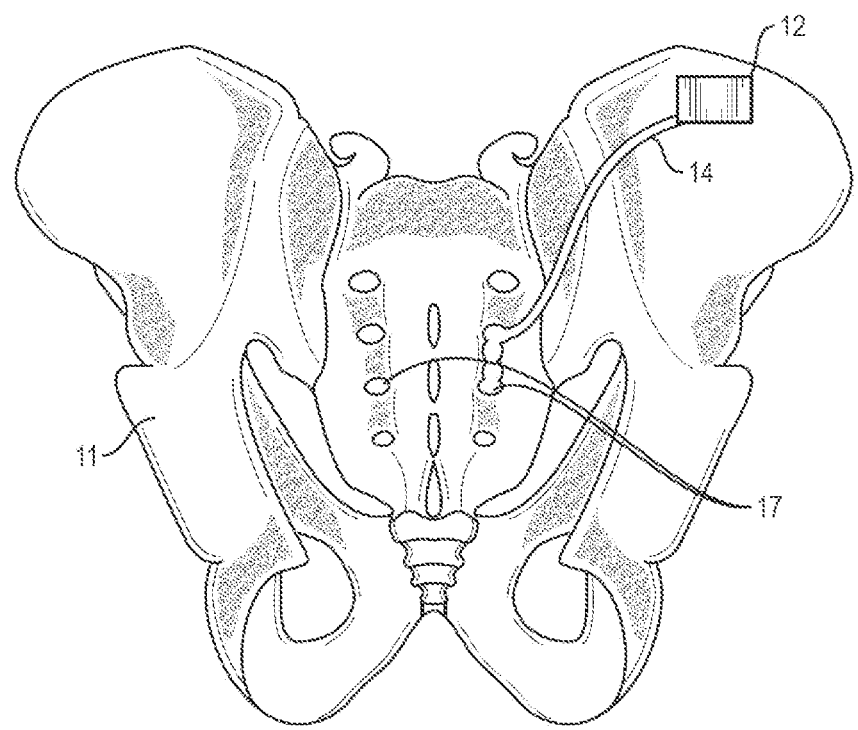

Such a system is schematically illustrated in FIGS. 1A and 1B, which shows front and back views, respectively, of a patient pelvic region, including the pelvic bone 11, bladder 13 and the sacrum, including the $3^{rd}$ sacral vertebrae 17. A bladder sensor, specifically, a pressure sensor 10 is provided as well as a unit 12 that houses a nerve current regulator and an electrical stimulator which sends and receives current to and from the sacral nerves via a lead 14, which in the example shown is inserted into the S3 foramen. A handheld control unit, not shown, may be used to control and/or monitor the pressure sensor, nerve current regulator and electrical stimulator, to gather data, and to change parameters, such as the intensity and frequency of stimulation or the degree of nerve current regulation, among other possible functions.

With regard to the bladder pressure sensing unit that is used to measure the pressure of the bladder as it is filling, such a unit may include, for example, a processor, memory, a communication interface, a power source, typically rechargeable, and a sensor (e.g., a piezoelectric sensor, capacitive sensor, etc.) for sensing bladder pressure. Implantable pressure sensors are known in the art. In this regard, see, e.g., U.S. Patent Pub. No. 20070027494 to Gerber and International Pat. No. WO2013169896A2 to Margot S. Damaser et al., the latter of which describes a wireless, catheter-free, battery-powered, rechargeable bladder pressure sensor. See also Joshua N. Weaver, et al., "Toward a Minimally Invasive Bladder Pressure Monitoring System: Model Bladder for In Vitro Testing" Proceedings of the 2010 3rd IEEE RAS & EMBS, International Conference on Biomedical Robotics and Biomechatronics, The University of Tokyo, Tokyo, Japan, Sep. 26-29, 2010. Implantable pressure sensors are also available from Tronics Group, 555 California Street, 3rd floor, San Francisco, Calif. USA, and provide miniature packaging compatible with heat sterilization, long-term stable pressure monitoring, static or waveform pressure acquisition, wired or wireless power and data transmission and includes a miniature MEMS capacitive pressure sensing element.

In a particular example, a wireless bladder pressure sensor may be provided with an attachment by which it can be secured to the bladder wall, and which may be inserted and secured using a cystoscope. This sensor may be configured to send signals periodically, send signals when prompted and/or send signals when the bladder pressure is at critical levels. In some examples, the bladder pressure sensor sends bladder pressure to an external memory to record the data collected.

In some examples, an electrical stimulator may be used to provide afferent signals to the brain. For example, in certain arrangements, a high level afferent signal may be sent when a signal is received (e.g., from a handheld device or a pressure sensor) that it is time to void the bladder. The afferent signal may be introduced via sacral nerves in certain examples. The electrical simulator device may include a lead having at least one stimulating electrode for applying stimulation to one or more nerves when the lead is positioned proximal (e.g., adjacent, around, within, etc.) the one or more nerves. In some examples, the lead may contain a number of stimulating electrodes to provide an option as to which electrodes may be stimulated for optimal results. The lead may include small barbs, called tines, which help to keep it in place and reduce movement of the lead, or the lead may include a cuff which is wrapped around the one or more nerves, among other possibilities. In certain examples, wireless electrodes may be used in the present disclosure, Where sacral nerves are to be simulated, they may be accessed, for example, via the S3 foramen or by another suitable route. As shown in the block diagram of FIG. 3, an electrical stimulation device 18 may include a lead 20, a processor 56, memory 58, an electrical stimulator 60, a communication interface 62, and a power source 64. The electrical stimulator 60 may be, for example, a stimulation pulse generator, as such devices are readily available and known in the art. Memory 58 may store, for example, instructions for execution, including instructions received via communication interface 62 from a remote device (e.g., pressure sensor, handheld communication device, etc.), updated stimulation parameters (e.g., regarding amplitude, pulse width, pulse rate, etc.), and a record of stimulation signals applied by the device. Processor 56 controls electrical stimulator 60 to deliver electrical stimulation, and communication interface 62 to send and receive information. In some arrangements, the electrical stimulator device may be, for example, a modified version of a commercially available stimulation device, which may be reconfigured to wirelessly receive signals, for example, from a bladder pressure sensor or external handheld device, and to send electrical pulses when prompted, instead of transmitting constant pulses.

In this way, an electrical stimulator may be provided that can apply or not apply stimulation current based on, for example, pressure readings, patient input, and so forth. When it is determined that it is time to void, the electrical stimulator can increase the intensity of afferent signals going to the brain, which may, for example, give the body the urge sensation, resulting in contraction of the detrusor muscles and relaxation of the external urinary sphincter.

A nerve current regulator may also be provided herein to monitor and control electrical signals traveling through one or more nerves of interest, for example, the sacral nerves. For example, in some arrangements, the nerve current regulator monitors afferent signals in one or more nerves. If the afferent signals are too low in intensity (e.g., they do not meet or exceed a predetermined lower signal threshold) steps can be taken to ensure that the current is increased to meet or exceed that threshold. More typically, the afferent signals will be too high in intensity (e.g., they may exceed a predetermined upper signal threshold), in which case steps may be taken to ensure that the signals are at least partially blocked such that the threshold is not exceeded. The nerve current regulator may include a lead having at least one sensing electrode for sensing the current in one or more nerves, for example, a lead having at least one sensing electrode adapted to sense the electroneurogram activity of the nerves. Devices for determining electroneurogram activity are known in the art. In some examples, the lead may contain a number of sensing electrodes to provide an option as to which electrode or electrodes may be sensed. As with the electrical stimulation lead, the lead for the nerve current regulator may include tines which help to keep it in place and reduce movement of the lead, or the lead may include a cuff which is wrapped around the nerve, among other possibilities. The sacral nerves may be accessed via the S3 foramen or by another suitable route.

In various examples, in addition to at least one sensing electrode, the nerve current regulator device also includes a lead having at least one signal modifying electrode adapted to modify the nerve signals transmitted by one or more nerves. In some examples, the lead may contain a number of signal modifying electrodes. As above, the lead may include tines, which help to keep it in place and reduce movement of the lead, or the lead may include a cuff which is wrapped around the nerve, among other possibilities, and the sacral nerves may be accessed, for example, via the S3 foramen or by another suitable technique. In some examples, sensing and modifying electrodes may be provided on separate leads, in other examples sensing and modifying electrodes may be provided on a single lead. In still other examples, sensing electrodes, signal modifying electrodes, and stimulating electrodes may be provided on a single lead. In certain examples, electrodes may provide multiple functions (e.g., sensing, modifying and stimulation functions). In this regard, it will be appreciated that the same electrode(s) may be employed for signal sensing, modification and stimulation.

In certain examples, electrical signals traveling through one or more nerves (e.g., the sacral nerves) may be modified through the creation of unidirectionally propagating action potentials. By way of background, under physiological conditions, a nerve action potential (AP) is generated at one end of an axon and proceeds towards its other end. Electrical nerve stimulation of an axon normally produces two propagating APs, one in the orthodromic direction (towards the terminal end where the neurotransmitter is released) and one propagating in the antidromic direction (towards the soma). Techniques have been developed to prevent an action potential from propagating in one of these directions, while allowing it to travel in the other. Such unidirectionally propagating APs may be used for collision block of naturally incoming afferent nerve signals being sent to the brain. In this regard, an electrically initiated AP can be sent towards an oncoming naturally generated AP (e.g., originating in the bladder) to at least partially neutralize the oncoming signal and provide an at least partial block. The stimulation frequency selected may depend, for example, on the distance of the stimulation site from the action potential generator, the conduction velocity of the axons, and the refractory period. Electrically initiated action potentials may be created using monopolar and multipolar (e.g., bipolar, tripolar, etc.) electrode arrangements. See, e.g., Case Western Reserve University; Department of Biomedical Engineering; Applied Neural Control: J. T. Mortimer, Homepage, Unidirectional propagation; N. Bhadra et al., "Selective block of external anal sphincter activation during electrical stimulation of the sacral anterior roots in a canine model," *Neurogastroenterol Motif.* 2005 October; 17(5): 721-6; J. D. Sweeney et al., "Acute animal studies on electrically induced collision block of pudendal nerve motor activity," *Neurouology and Urodynamics*, Volume 8, Issue 5, pages 521-536, 1989; and Ira J. Ungar et al., "Generation of unidirectionally propagating action potentials using a monopolar electrode cuff," *Annals of Biomedical Engineering,* 1986, Volume 14, Issue 5, pp 437-450.

Figure 4:
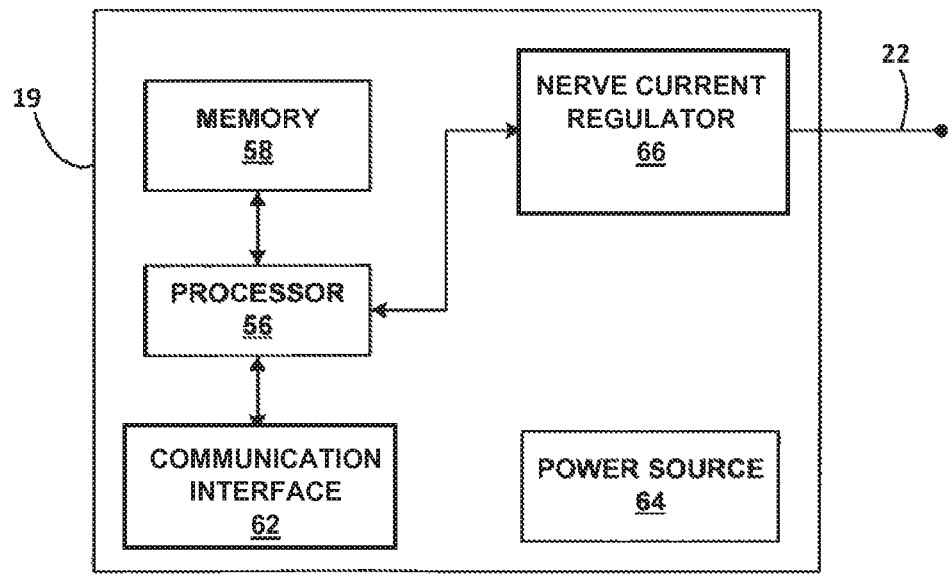
FIG. 4 is functional block diagram illustrating various components of an exemplary implantable regulating device, in accordance with an example of the present disclosure.

As shown in the block diagram of FIG. 4, a nerve current regulating device 19 may include at least one lead 22, a processor 56, memory 58, a nerve current regulator 66 (which includes circuitry for nerve current measurement and control, for example, control by at least partial blocking of afferent signals via electrically initiated unidirectionally propagating APs), a communication interface 62, and a power source 64. The memory 58 may store, for example, instructions for execution, including instructions received via communication interface 62 from a remote device (e.g., pressure sensor, handheld communication device, etc.), updated control parameters (e.g., blocking signal frequency and amplitude), and a record of control signals applied by the device. Processor 56 controls communication interface 62 to send and receive information and controls nerve current regulator 66 to measure nerve current and deliver control signals (e.g., electrically initiated unidirectionally propagating APs).

Figure 3:
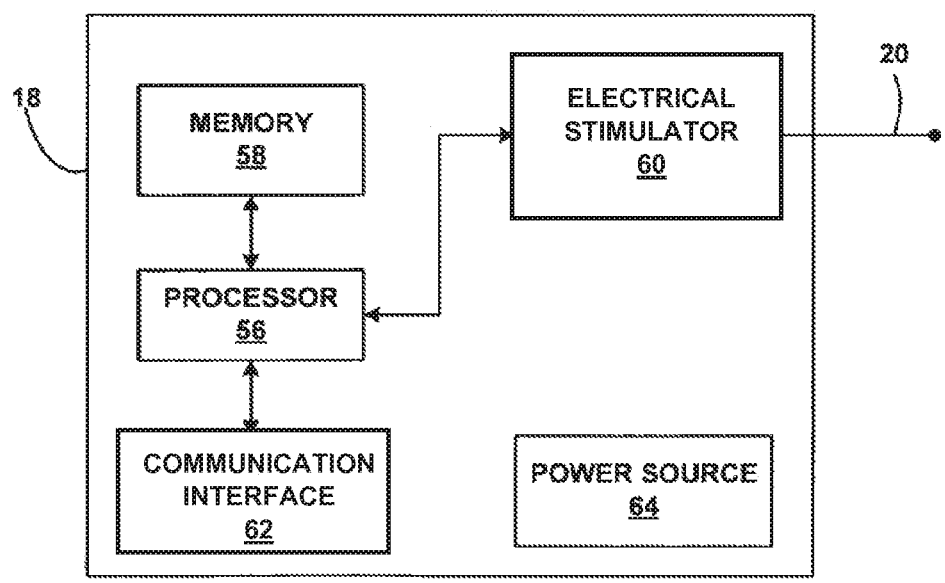
FIG. 3 is functional block diagram illustrating various components of an exemplary implantable stimulating device, in accordance with an example of the present disclosure.
Figure 5:
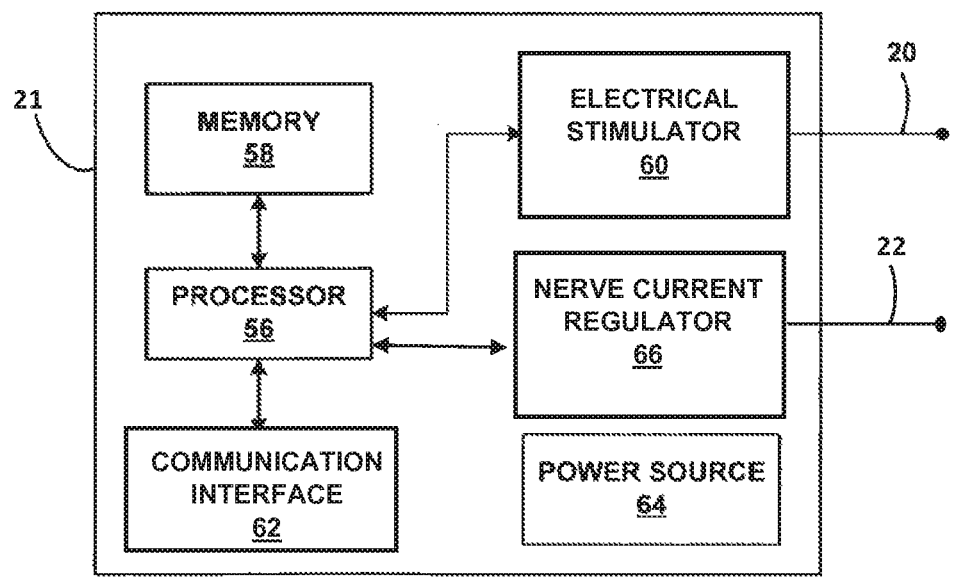
FIG. 5 is functional block diagram illustrating various components of an exemplary implantable regulating and stimulating device, in accordance with an example of the present disclosure.

In certain examples, the devices of FIGS. 3 and 4 may be combined into a single device like that shown in the block diagram of FIG. 5 which includes, a processor 56, memory 58, electrical stimulator 60, lead 20, nerve current regulator 66, lead 22, communication interface 62, and power source 64, whose functions are discussed above. In certain examples, a single lead may be employed to provide sensing, modification, and stimulation functions.

In some arrangements, in cases where the natural afferent signals in the sacral nerve are erroneously elevated, the signals may be partially blocked to create low level signals mimicking low level afferent signals that normally are sent during bladder filling. In other arrangements, erroneously elevated natural afferent signals in the sacral nerve may be substantially completely blocked and replaced by artificial electrical signals mimicking low level afferent signals that normally are sent during bladder filling. Such signals may be provided by using an electrical stimulator like that discussed above modified to send low level signals. Natural afferent signals may be partially or substantially completely blocked through the creation of unidirectionally propagating action potentials as discussed above or by another suitable technique, such as that described in U.S. Pat. No. 7,389,145, which describes blocking nerve impulses using an implanted lead electrode located proximate a nerve, wherein a specific waveform is used that causes the nerve membrane to become incapable of transmitting an action potential.

By having the ability to monitor and modify the current associated with the electric signals traveling through nerves such as the sacral nerves, the nerve current regulator device can ensure that proper afferent signals are being relayed to the brain (e.g., by keeping the nerve current low), thereby avoiding a premature increase of the intensity of afferent signals that cause a sudden urge to urinate.

The external handheld control unit may be a small battery-powered, typically rechargeable, portable device that accompanies a patient throughout a daily routine. The external handheld control unit may have a display, for example, a liquid crystal (LDC) or light emitting diode (LED) screen and a simple user interface, such as a button, keypad or touchscreen (e.g., a resistive or capacitive touchscreen). In various examples, a programmable external handheld control unit may be used to monitor and/or activate any of the pressure sensor, nerve current regulator and/or electrical stimulator. It may wirelessly receive signals from any of the sensor, regulator and stimulator, and may be configured to show the user the current settings and pressure readings. The user may be able to adjust certain parameters, such as the intensity of the stimulation or level of afferent signal suppression. The external handheld control unit may also receive bladder pressure information from the pressure sensor, nerve current information from the regular, or both, and transmit command signals to the regulator to adjust the nerve current regulation parameters, to adjust stimulation parameters, or both. The user may also be able to input a desire or approval to void the bladder, whether prompted or unprompted. The user may be prompted, for example, in conjunction with a routine such as that discussed below in conjunction with FIG. 2. The user may initiate a voiding event, i.e., a voluntary voiding of bladder, via the user interface provided by the external handheld control unit. In some examples, the length of time for a voiding event may be determined by providing input (e.g., via a button or touchscreen) throughout the duration of avoiding event, by providing input a first time to initiate voiding and a second time when voiding is complete, or by voiding for a predetermined length of time.

Figure 2:
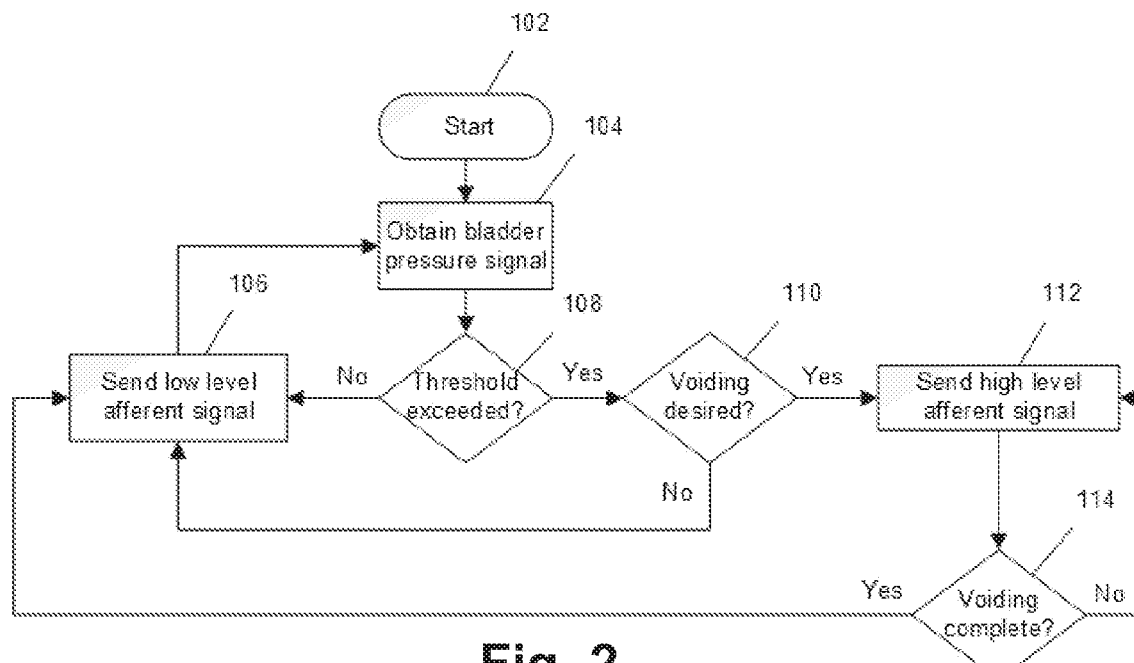
FIG. 2 is a flow chart illustrating a technique for delivery of stimulation therapy, in accordance with an example of the present disclosure.

A process in accordance with certain examples of the disclosure will now be discussed in conjunction with FIG. 2. Once the process is started 102, a bladder pressure signal is obtained 104, for example, by the handheld control unit. The control unit then determines whether or not the bladder is sufficiently full to initiate a voiding event, for example, by comparing the pressure signal being received to a predetermined threshold value 108, which may vary from patient to patient. If the bladder is not sufficiently full to initiate a voiding event (e.g., because the pressure signal being received is less that the threshold value 108), a steps are taken to ensure that a low level afferent signal is sent to the brain 106 (e.g., by means of a nerve current regulator described herein). After a predetermined interval, the bladder pressure signal is again obtained by the controller, at which point it is again determined whether or not the bladder is sufficiently full to initiate a voiding event. Once enough urine has flowed into the bladder, it may be determined that the bladder is sufficiently full to initiate a voiding event (e.g., because the signal being received from the pressure sensor exceeds the threshold value) at which point the patient may be prompted as to whether or not voiding is desired 110. If the patient does not respond or indicates that it is not a good time to void, a low level afferent signal continues to be sent to the brain 106 and the pressure continues to be monitored. The patient may be reminded periodically that the bladder is sufficiently full to be voided and queried as to whether or not voiding is desired. Once the patient indicates that voiding is desired, steps may be taken to ensure that a high level afferent signal is sent to the brain 112 (e.g., by removing a block being applied to a natural afferent signal and/or by means of electrical stimulation), allowing the patient to void. The patient is then asked whether voiding is complete 114. If a negative response is provided, or in the absence of a response, a high level afferent signal is continued to be sent to the brain. Once, the patient indicates that voiding is complete (or alternatively a predetermined amount of time for voiding has elapsed), steps may be once again taken to ensure that a low level afferent signal is once again sent to the brain 106, and the process repeated.

Although various examples are specifically illustrated and described herein, various modifications and variations of the present disclosure are covered by the above teachings and are within the purview of the appended claims without departing from the spirit and intended scope of the present disclosure. For example, in some arrangements, electrical stimulator and pressure sensor may be provided in a single device attached to the bladder which wirelessly communicates with the nerve current regulator. In certain of these arrangements, the stimulator may stimulate the bladder directly, rather than, for example, the sacral nerves. In some arrangements, the nerve current regulator may monitor and control signals within the hypogastric nerves, rather than the sacral nerves. In some arrangements, the system and methods of the present disclosure may be modified to ensure urinary retention. In some arrangements, nerve signals associated with the external sphincter may be monitored and controlled, in which case the afferent signals sent to the brain may be kept high while the bladder is filling and low during urination.

While principles of the present disclosure are described herein with reference to illustrative examples for particular applications, it should be understood that the disclosure is not limited thereto. Those having ordinary skill in the art and access to the teachings provided herein will recognize additional modifications, applications, examples, and substitution of equivalents all fall within the scope of the examples described herein. Accordingly, the disclosure is not to be considered as limited by the foregoing description.

We claim:

1. A method of treating a patient comprising:
   (a) measuring current within one or more nerves of the patient;
   (b) sensing bladder pressure within a urinary bladder of the patient; and
   (c) forming modified electrical signals within the one or more nerves based on measured current and sensed bladder pressure obtained in (a) and (b),
   wherein the modified electrical signals comprise natural afferent signals within the one or more nerves that are at least partially blocked, and wherein the natural afferent signals in the one or more nerves are at least partially blocked in response to a condition wherein the measured current is below a predetermined threshold.

2. The method of claim 1, wherein the modified electrical signals comprise artificial signals that are introduced into the one or more nerves.

3. The method of claim 1, wherein natural afferent signals in the one or more nerves are unblocked in response to conditions that comprise a condition wherein the sensed pressure is above a predetermined threshold.

4. The method of claim 1, wherein artificial afferent signals are introduced into the one or more nerves in response to conditions comprising a condition wherein the sensed pressure is above a predetermined threshold.

5. The method of claim 1, further comprising transmitting information regarding the sensed pressure and information regarding the measured current to a handheld device that controls an implanted nerve current regulator based on the information.

6. The method of claim 1, wherein the patient is treated for overactive bladder.

7. The method of claim 1, wherein the step of forming modified electrical signals within the one or more nerves includes at least partially blocking electrical signals generated by the bladder and transmitted by the one or more nerves.

8. The method of claim 7, wherein the at least partially blocking of electrical signals includes forming unidirectionally propagating action potentials within the one or more nerves.

9. The method of claim 1, wherein the step of forming modified electrical signals within the one or more nerves includes delivering a high level afferent signal to one or more electrodes to stimulate voiding of the bladder.

10. The method of claim 1, further comprising an initial step of attaching the bladder pressure sensor to a surface of the bladder with at least one barb or tine.

11. A method of treating a patient, comprising:
    measuring a bladder pressure of a bladder with a bladder pressure sensor;
    sensing an electrical signal generated by the bladder and transmitted by one or more nerves; and
    at least partially blocking the electrical signal transmitted by the one or more nerves by forming unidirectionally propagating action potentials within the one or more nerves based on the bladder pressure measured by the bladder pressure sensor.

12. The method of claim 11, further comprising regulating the electrical signal transmitted by the one or more nerves by delivering a high level afferent signal to one or more electrodes in the bladder.

13. The method of claim 11, further comprising an initial step of attaching the bladder pressure sensor to an inner surface of the bladder with at least one barb or tine.

14. The method of claim 11, further comprising stimulating one or more electrodes positioned within the bladder to introduce stimulating electrical signals into the one or more nerves.

15. The method of claim 11, further comprising an initial step of implanting a single implantable device on or within the bladder, wherein the single implantable device includes a nerve current regulator having electrodes and an electrical stimulator having electrodes, and wherein the electrodes of both the nerve current regulator and the electrical stimulator are provided on a single lead.

16. The method of claim 15, further comprising inputting into a control unit a signal to cease blocking the electrical signals transmitted by the one or more nerves via the unidirectionally propagating action potentials, and inputting into the control unit a user input indicating that a voiding of the bladder is complete, wherein the input that the voiding of the bladder is complete causes the nerve current regulator and electrical stimulator to ensure that low level afferent signals are transmitted through the one or more nerves.

17. A method of treating a patient, comprising:
    measuring a bladder pressure of a bladder with a bladder pressure sensor;
    sensing an electrical signal generated by the bladder and transmitted by one or more nerves;
    at least partially blocking the electrical signal transmitted by the one or more nerves by forming unidirectionally propagating action potentials within the one or more nerves with one or more electrodes based on the bladder pressure measured by the bladder pressure sensor to mimic low level afferent signals; and
    delivering a high level afferent signal to the one or more electrodes to stimulate voiding of the bladder.

18. The method of claim 17, wherein the delivery of the signals to the one or more electrodes is regulated by at least one control unit in communication with the bladder pressure sensor.

19. The method of claim 18, wherein the at least one control unit signals a user interface to display one or more prompts for at least one input comprising an approval to initiate the delivery of the high level afferent signal to stimulate voiding of the bladder.

20. The method of claim 19, wherein upon receiving the approval, the control unit is configured to signal a nerve current regulator to cease blocking afferent signals via unidirectionally propagating action potentials and is further configured to signal an electrical stimulator to increase the intensity of the afferent signals; and wherein the control unit is further configured to receive an input indicating that the voiding is complete, and wherein in response to the input indicating that the voiding is complete, the control unit is configured to signal the nerve current regulator and an electrical stimulator to ensure that low level afferent signals are transmitted through the at least one nerve.

* * * * *